United States Patent [19]

Turner

[11] Patent Number: 5,407,589
[45] Date of Patent: Apr. 18, 1995

[54] FABRIC SOFTENING COMPOSITION

[75] Inventor: Graham A. Turner, Wirral, United Kingdom

[73] Assignee: Lever Brothers Company, Division of Conopco, Inc., New York, N.Y.

[21] Appl. No.: 170,351

[22] PCT Filed: Jun. 30, 1992

[86] PCT No.: PCT/GB92/01181
§ 371 Date: Apr. 29, 1994
§ 102(e) Date: Apr. 29, 1994

[87] PCT Pub. No.: WO93/01265
PCT Pub. Date: Jan. 21, 1993

[30] Foreign Application Priority Data

Jul. 5, 1991 [GB] United Kingdom ............... 9114540

[51] Int. Cl.$^6$ ............................................ D06M 13/46
[52] U.S. Cl. ................................ 252/8.8; 252/8.6; 252/8.9; 252/547
[58] Field of Search ................ 252/8.6, 8.8, 8.9, 547

[56] References Cited

U.S. PATENT DOCUMENTS

| 4,137,180 | 1/1979 | Naik et al. | 252/8.8 |
| 5,288,417 | 2/1994 | Bauer et al. | 252/8.8 |

FOREIGN PATENT DOCUMENTS

| 0239910 | 10/1987 | European Pat. Off. |
| 0409502 | 1/1991 | European Pat. Off. |
| 0409504 | 1/1991 | European Pat. Off. |
| 0420465 | 4/1991 | European Pat. Off. |
| 0486113 | 5/1992 | European Pat. Off. |
| 585040 | 3/1994 | European Pat. Off. |
| 2356627 | 1/1978 | France |
| 1048197 | 11/1966 | United Kingdom |
| 21291 | 10/1993 | WIPO |
| 9401168 | 8/1994 | WIPO |

Primary Examiner—Paul Lieberman
Assistant Examiner—Michael P. Tierney
Attorney, Agent, or Firm—A. Kate Huffman

[57] ABSTRACT

A fabric softening material comprising an ester-linked amine compound and/or its corresponding quaternary ammonium compound of general formula I.

$$\begin{array}{c} R_1 \\ | \\ N-(CH_2)_n-CH-(CH_2)_m-CH_2OOCR_2 \\ | \quad\quad\quad\quad | \\ R_1 \quad\quad\quad OOCR_2 \end{array} \quad (I)$$

where each $R_1$ group is independently selected from $C_{1-4}$ alkyl, alkenyl, or hydroxyalkyl groups; each $R_2$ group is independently selected from $C_{8-28}$ or alkenyl groups and n and m are integers from 1 to 5; such that the material has an Iodine value of between 5 and 24, preferably between 5 and 20. The invention also comprises an aqueous fabric softening composition containing the softening material.

5 Claims, No Drawings

FABRIC SOFTENING COMPOSITION

This invention relates to a fabric softening material and to a metzhod for its preparation. In particular the invention relates to a fabric softening composition for use in the rinse step of a fabric washing process.

Conventional rinse added fabric softening compositions contain fabric softening materials which are substantially water-insoluble cationic materials usually having two long alkyl chains. Typical of such materials are disteary dimethyl ammonium chloride. These materials are usually prepared in the form of.an aqueous dispersion or emulsion.

It has been proposed in EP 239 910 (PROCTER & GAMBLE) to incorporate ester linked quaternary ammonium compounds in fabric softening compositions. U.S. Pat. No. 3,915,867 (STEPAN) discloses the use of N-methyl, N,N-di(beta-$C_{14-18}$ acyloxyethyl) N-beta-hydroxy ethyl ammonium methosulphate in softening compositions. Other ester linked softener materials are described in U.S. Pat. No. 4,137,180 (LEVER BROTHERS). Softener materials comprising ester linkages are especially preferred for use in fabric conditioning compositions for environmental reasons.

A problem with quaternary softener materials comprising ester linkages is that some tend to have a relatively high pour point. Pour point can be defined as the lowest temperature at which a material can be observed to flow under specified conditions. (As explained in The Analysis of Fats and Oils by V C Mehlenbacher, The Garrard Press, Champaign, Ill. 1960). A high pour point renders the softener materials sometimes difficult to process. For example, the softener materials as described in U.S. Pat. No. 4,137,180 (LEVER BROTHERS) have high pour points meaning that they are hardly pumpable at temperatures conventionally used in rinse conditioner manufacture, eg. 60° C., and are difficult to disperse in water.

We have now found that the pour point of ester-linked softening materials can be lowered by using a higher proportion of unsaturated substituents in each molecule 10 compared with that normally used. The man skilled in the art would expect a decrease in softening performance from such materials since this phenomenon is seen with conventional quaternaries having two long alkyl chains. Surprisingly we have found that ester-linked quaternary ammonium compounds or their corresponding amines comprising a high proportion of unsaturated substituents in the molecule or mixture of molecules having unsaturated substituents with molecules having saturated substituents can give superior softening when compared to the softening performance obtained from saturated ester-linked quaternaries or their corresponding amines or non-ester-linked quaternaries.

In EP 0 052 517 (PROCTER & GAMBLE) it is disclosed that pourable, concentrated fabric softener compositions can be obtained when the composition comprises a mixture of a mono nitrogen quaternary ammonium salt, a di(2-amidoethyl) methyl quaternary ammonium salt and an imidazolinium salt where the cationic system has an Iodine value of at least 4.2. In this prior art specification the 'pourability' is defined in terms of the finished composition and not the component parts. No mention of ester-linked quaternaries or improved softening performance is made.

In JP 2169769A KAO CORP it is disclosed that softening and finishing agents for treating garments can comprise certain quaternary ammonium compounds with substituents having certain degrees of unsaturation.

Accordingly the present invention provides a fabric softening material comprising an ester-linked amine compound and/or its corresponding quaternary ammonium compound. The amine compound has a of general formula I

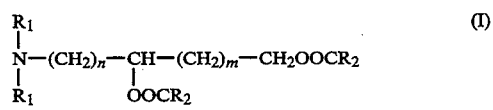

where each $R_1$ group is independently selected from $C_{1-4}$ alkyl, alkenyl or hydroxyalkyl groups; and each $R_2$ group is independently selected from $C_{8-28}$ alkyl or alkenyl groups, n is an integer from 0 to 5 and m is an integer from 1 to 5; such that the material has an Iodine value of between 5 and 24.

The quaternary ammonium compound corresponding to the ester-linked amine compound of Formula I has a Formula

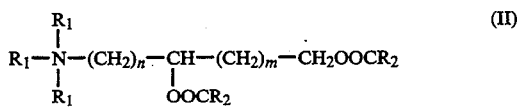

The advantages of fabric softening materials according to the invention are that they can have a lower pour point than ester-linked materials of lower Iodine value and can give superior softening than ester-linked materials of lower Iodine value.

Preferably the fabric softening material comprises at least 80% by weight of ester-linked amine and/or quaternary ammonium compound, and more preferably at least 90%. Most preferably the fabric softening material comprises between 80% and 95% by weight of ester-linked amine and/or quaternary ammonium compound.

Preferably the fabric softening materials of the invention comprise an extender material selected from:
  (a) tertiary amine or quaternary ammonium compounds comprising one long alkyl or alkenyl group with more than ten carbon atoms;
  (b) predominantly unbranched linear nonionic materials; and
  (c) mixtures thereof
since these extender materials have also been found to lower the pour point of ester-linked quaternary ammonium compounds as disclosed in EP 409 504 (Unilever).

The ester-linked quaternary ammonium compounds useful in the present invention are preferably prepared in the presence of more than a 10 mole % excess of alkyl or alkenyl groups as disclosed in EP 420 465 (Unilever) since this has also been found to lower the pour point of the compound.

Preferably the fabric softening material has an Iodine value between 5 and 20, most preferably between 5 and 15. Iodine value as used in the context of the present invention refers to the measurement of the degree of unsaturation present in a material by a method of nmr spectroscopy as described in Anal. Chem., 34, 1136 (1962) Johnson and Shoolery.

Iodine value is defined as the number of grams of iodine absorbed per 100 g of the test material. Olefinic materials absorb 1 gram of iodine per atom of olefinic hydrogen. Hence measurement can be converted to the equivalent Iodine Value. The hydrogen nmr spectrum at 360 MHz is obtained for the test material. The integral intensity, $I_s$, of the band derived from olefinic hydrogen in the alkyl chain and the integral intensity, $I_m$, of the band derived from terminal methyl groups in the alkyl chains are measured.

The number of olefinic hydrogens per molecule is given by:

$$\frac{I_s}{I_m} \times 6$$

and the Iodine Value is given by:

$$\frac{I_s \times 127 \times 100 \times 6}{I_m \times MMW}$$

where MMW is the mean molecular weight of the test material.

Preferred fabric softening materials comprise a 1:4 parts by weight mixture of 1,2 ditallowyl oxy-3-trimethylammoniopropane chloride made according to U.S. Pat. No. 4,137,180 (Lever Bros.) with its dihardened tallowy counterpart.

Tallow fatty acids have a chain length distribution of $C_{14}$ of 5%, $C_{16}$ of 30%, $C_{18}$ (saturated) of 20% and $C_{18}$ (unsaturated) of 45% as known in the art and also described in Naik (U.S. Pat. No. 4,137,180) herein incorporated by reference.

A second aspect of the invention provides an aqueous fabric softening composition comprising a fabric softening material comprising an ester-linked amine compound of formula I and/or its corresponding quaternary ammonium compound wherein the compound comprises at least one unsaturated substituent such that the material has an Iodine value of between 5 and 24.

Preferably the composition comprises from 5% to 80% by weight of fabric softening material, more preferably from 15% to 60% by weight. Compositions of the invention are obtainable by heating the material to a temperature above 40° C. followed by dispersing the material into water. Preferably the materials are heated to a temperature of above 50° C. and dispersed in water at elevated temperature.

The compositions of the invention preferably have a pH of more than 2.0 and less than 8.0, more preferably less than 5.0. Especially preferred are pH values in the range of from 2.5 to 4.0.

Compositions of the invention may in addition to the above ingredients also comprise other ingredients, such as non-aqueous solvents such as $C_{1-4}$ alkanols and polyhydric alcohols, pH-buffering agents such as weak acids e.g. phosphoric, benzoic or citric acids, re-wetting agents, viscosity modifiers, aluminium chlorohydrate, anti-gelling agents, perfumes, perfume carriers, hydrocarbons, fluorescers, colourants, hydrotropes, antifoaming agents, antiredeposition agents, enzymes, optical brightening agents, opacifiers, stabilisers such as guar gum and polyethylene glycol, anti shrinking agents, anti-wrinkle agents, silicones, soil release agents, antioxidants, anti-corrosion agents, preservatives, dyes, bleaches, bleach precursors, drape-imparting agents, antistatic agents and ironing aids.

The invention will be further illustrated by means of the following examples:

EXAMPLE 1

The following compositions were prepared by melting the required amounts of unsaturated compound and saturated compound, mixing and adding the premix to hot (70° C.) demineralised water while stirring.

The softening performance of the monitors was tested by treating 40 g of terry monitors with a 2 ml dose of a 5% dispersion of the mix in 1 liter of water, line drying and assessing for softness using an expert panel and a round robin paired comparison technique.

| Softening Material | Iodine Value | Softness Score |
|---|---|---|
| Arquad 2T | 42 | 0.16 |
| 4:1 2T/2HT | 33 | 0.27 |
| 2:1 2T/2HT | 28 | 0.10 |
| 1:2 2T/2HT | 14 | 0.24 |
| 1:4 2T/2HT | 8 | 0.00 |
| Arquad 2HT | 0 | 0.33 |

Higher softness scores denote softer monitors. A difference of 0.45 between scores indicates a significant difference at the 95% confidence limit.

Arquad 2T is ditallow dimethyl ammonium chloride ex Akzo Chemie.

Arquad 2HT is dihardened tallow dimethyl ammonium chloride ex Akzo Chemie.

These results show that mixing conventional quaternary ammonium compounds to iodine values of 42 does not produce a significant increase in softening performance.

EXAMPLE 2

Compositions were prepared and softening assessed as described in Example 1.

| Softening Material | Iodine Value | Softness Score |
|---|---|---|
| T TMAPC | 26 | −0.75 |
| 4:1 T/HT | 29 | −0.39 |
| 2:1 T/HT | 24 | 0.02 |
| 1:2 T/HT | 12 | 0.19 |
| 1:4 T/HT | 7 | 0.76 |
| 1:8 T/HT | 5 | 0.38 |
| HT TMAPC | 0 | −0.21 |

A difference of 0.62 between scores indicates a significant difference at the 95% confidence limit.

T TMAPC is 1,2 ditallowyloxy-3-trimethylammoniopropane chloride ex Hoescht.

HT TMAPC is 1,2 dihardened tallowyloxy-3-trimethylammoniopropane chloride ex Hoescht.

These results show that mixing ester-linked quaternary ammonium compounds to give a material with an Iodine value of between 5 and 24 leads to an increase in softening performance.

EXAMPLE 3

5% by weight dispersions of 4:1 mixtures of hardened tallow quaternary ammonium material to soft tallow quaternary ammonium material were prepared by co-melting the materials and adding the premix to hot water (70° C.) with stirring. The dispersions were cooled to room temperature with stirring. 2 ml of the dispersions were added to 1 of 14° FH water containing 0.001% of alkyl benzene sulphonate to simulate anionic carry over from the main wash. Three test monitors (40–50 g terry towelling) were placed in the dispersions and agitated in a tergotometer (5 mins, 60 rpm). The monitors were line dried and softening assessed using a round robin paired comparison.

| Mixtures | Iodine Value | Softness Score |
|---|---|---|
| 5% Arquad 2HT | 0 | 1.12 |
| 5% 4:1 Arquad 2HT:Arquad 2T | 8 | 0.63 |
| 5% 4:1 Tetranyl AHT-1:AT-1 | 5 | 0.00 |
| 5% 4:1 HT TMAPC:T TMAPC | 7 | 1.38 |
| 5% 4:1 Rewoquat W75H:W75 | — | 0.73 |

Rewoquat W75H is dishardened tallow imidazolinium quaternary.

Rewoquat W75 is ditallow imidazolinium quaternary.

Tetranyl AT-1 is N-methyl, N,N di($\beta$-tallowyloxy ethyl) N $\beta$-hydroxyethyl ammonium chloride ex Kao.

Tetranyl AHT-1 is N-methyl, N,Ndi ($\beta$-hardened tallowyloxy ethyl) N $\beta$-hydroxyethyl ammonium chloride ex Kao.

These results show that at the 95% significance level, mixtures of hard and soft 1,2 di-tallowyloxy-3-trimethylammonio propane chloride give better softening performance than all the other mixtures tested.

I claim:

1. A fabric softener comprising a material selected from the group consisting essentially of an ester-linked amine compound of Formula I

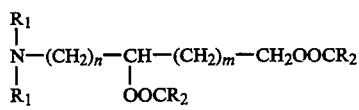

or a quaternary ammonium compound corresponding to the ester-linked amine compound having a formula

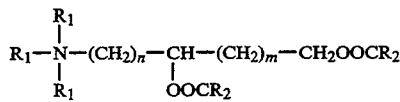

or mixtures thereof,
wherein each $R_1$ group is independently selected from $C_{1-4}$ alkyl, alkenyl or hydroxyalkyl groups; each $R_2$ group is independently selected from $C_{14}$–$C_{18}$ or alkenyl groups and n and m are integers from 1 to 5, the material having an iodine value of between 5 and 12, and the ratio of unsaturated substituents to saturated substituents represented by the $R_2$ group is 1:2 to 8 unsaturated to saturated substituents.

2. A fabric softener according to claim 1 wherein the material has an iodine value between 7 and 12.

3. A fabric conditioner according to claim 1 wherein the material comprises 1 part by weight of 1,2 ditallowoxyloxy-3-trimethylammoniopropane chloride with 4 parts of 1,2 dihardened tallowyloxy-3-trimethylammoniopropane chloride.

4. An aqueous fabric softening composition as claimed in claim 1 wherein the pH lies between 2 and 8.

5. An aqueous fabric softening composition comprising:

(a) a fabric softener selected from the group consisting essentially of an ester-linked amine compound of Formula

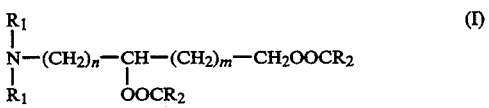

or a quaternary ammonium compound corresponding to the ester-linked amine compound having a formula

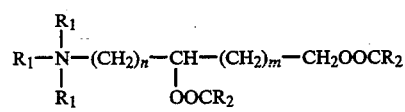

or mixtures thereof,
wherein each $R_1$ group is independently selected from $C_{1-4}$ alkyl, alkenyl or hydroxyalkyl groups; each $R_2$ group is independently selected from $C_{14}$–$C_{18}$ or alkenyl groups and n and m are integers from 1 to 5, the material having an iodine value of between 5 and 12, and the ratio of unsaturated substituents to saturated substituents represented by the $R_2$ group is 1:2 to 8 unsaturated to saturated substituents; and (b) an effective amount of water.

* * * * *